Figure 1:
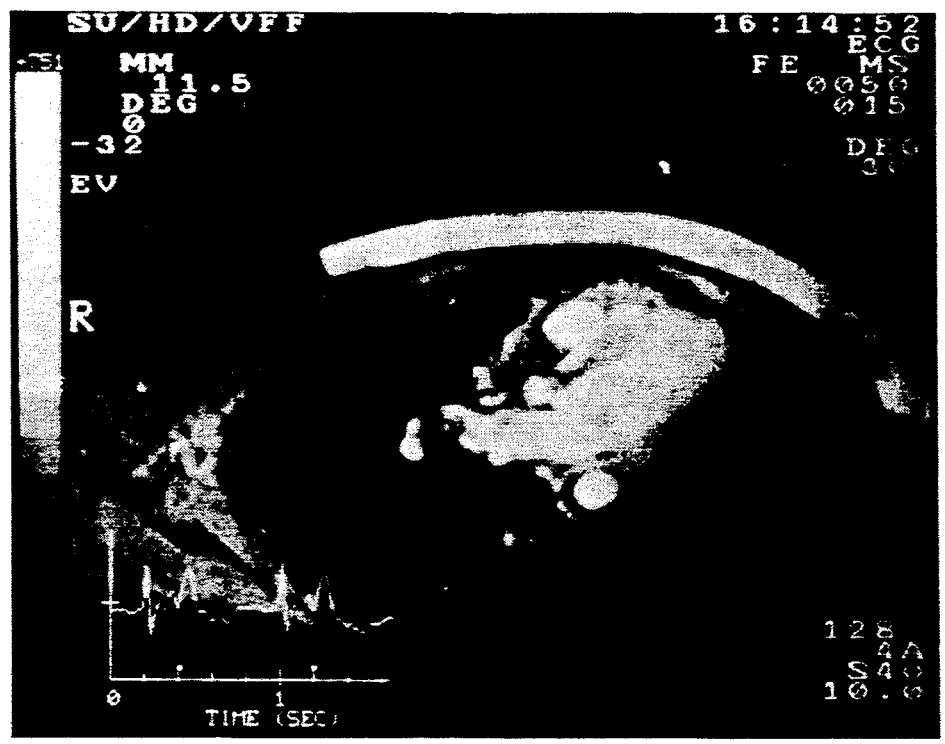

United States Patent [19]

Suga et al.

[11] Patent Number: 5,219,653
[45] Date of Patent: Jun. 15, 1993

[54] SHEET FOR ASSISTING IN NMR DIAGNOSIS

[75] Inventors: Daisaku Suga, Kakogawa; Tsunemitsu Matsuda, Kobe; Shozo Tanioku, Nara; Kenji Takeuchi, Osaka, all of Japan

[73] Assignee: Arakawa Chemical Industries, Ltd., Osaka, Japan

[21] Appl. No.: 797,509

[22] Filed: Nov. 22, 1991

[30] Foreign Application Priority Data

Nov. 27, 1990 [JP] Japan .................. 2-326583
Jun. 10, 1991 [JP] Japan .................. 3-236756

[51] Int. Cl.⁵ .......................... B32B 1/00
[52] U.S. Cl. ............. 428/332; 428/500; 428/522; 524/845
[58] Field of Search ........... 428/500, 332, 522; 524/845

[56] References Cited

FOREIGN PATENT DOCUMENTS

| 0106551 | 4/1984 | European Pat. Off. . |
| 3614142 | 11/1986 | Fed. Rep. of Germany . |
| 60-032830 | 2/1985 | Japan . |
| 63-242345 | 1/1988 | Japan . |
| 2-62902 | 9/1990 | Japan . |

*Primary Examiner*—Edith Buffalow
*Attorney, Agent, or Firm*—Armstrong, Westerman, Hattori, McLeland & Naughton

[57] ABSTRACT

The present invention provides an NMR diagnosis assisting sheet characterized in that the sheet comprises a molded body of a water-absorbing resin, the water-absorbing resin forming a uniform matrix phase wherein the molecules of the resin are interlocked with one another, and water absorbed by the resin is uniformly dispersed as chemically and/or physically bonded to the resin.

6 Claims, 1 Drawing Sheet

SHEET FOR ASSISTING IN NMR DIAGNOSIS

The present invention relates to a novel sheet for assisting in NMR diagnosis.

Nuclear magnetic resonance (NMR) images are utilized in recent years in diagnosing lesions, bloodstreams, etc. in the living body. However, since NMR images are formed by the magnetic data obtained by exciting protons in the structure of the living body with high frequency waves, difficulty has been encountered in obtaining sharp images of organs, such as the heart and liver, wherein the blood flows briskly in a complex fashion.

An object of the present invention is to provide a novel assisting sheet which is suitably usable in NMR diagnosis.

Another object of the present invention is to provide a novel NMR diagnosis assisting sheet which makes it possible to obtain sharp NMR images of internal portions of the living body, especially of the heart, liver and like organs wherein the blood flows briskly in a complex manner.

These and other objects of the present invention will become apparent from the following description.

The present invention provides an NMR diagnosis assisting sheet characterized in that the sheet comprises a molded body of a water-absorbing resin, the water-absorbing resin forming a uniform matrix phase wherein the molecules of the resin are interlocked with one another, and water absorbed by the resin is uniformly dispersed as chemically and/or physically bonded to the resin.

In view of the foregoing situation, we have conducted intensive research and found the novel fact that when a sheet comprising a molded body of a water-absorbing resin of specified structure is used in NMR diagnosis, very sharp NMR images can be obtained which reproduce the internal state of the living body. The present invention has been accomplished based on the novel finding.

The NMR diagnosis assisting sheet of the present invention essentially comprises a molded body of a water-absorbing resin having the structure specified above.

The molded body of water-absorbing resin of the present invention is in its entirety in the form of a uniform matrix phase wherein the molecules of the resin are interlocked with one another. This means that the water-absorbing resin forming the molded body is formed by a single gel wherein molecular chains of the resin are present as interlocked with one another. The resin has water absorbed thereby and uniformly dispersed in the matrix phase, as chemically and/or physically bonded with the resin. The term "chemically bonded" refers to a hydrogen bond between the water-absorbing resin and the dispersed water. The term "physically bonded" refers to so-called free water not associated, for example, with the hydrogen bond and taken into the water-absorbing resin in a stable state energetically.

The molded body of the water-absorbing resin for use in the present invention may have air bubbles insofar as they do not deform the sheet. Usually the amount of air bubbles should not exceed about 30 vol. % of the molded body. Preferably, the molded body is substantially free from air bubbles from the viewpoint of obtaining sharper NMR images. The expression "substantially free from air bubbles" means that no air bubbles are observable with the unaided eye. More specifically stated, it is desired that the number of air bubbles up to about 0.1 mm in diameter be not greater than about 3 per cm$^3$ of the molded body.

To obtain sharper NMR images, it is also desired that the molded body of water-absorbing resin of the invention be at least 5 mm in thickness, more desirably about 1 to about 3 cm in thickness.

The water-absorbing resin to be used for the molded body of the invention is preferably a crosslinked product of an acrylic acid polymer or a crosslinked product of a polymer of alkali metal salt of acrylic acid, which can be produced advantageously, for example, by the following processes.

(1) A process wherein a mixture of a photoinitiator and an aqueous monomer solution containing acrylic acid and/or an alkali metal salt of acrylic acid, and a crosslinking agent is cooled, solidified and molded, and the molded mixture is irradiated with ultraviolet rays to polymerize and crosslink the mixture.

(2) A process wherein a mixture of a photoinitiator and an aqueous monomer solution containing acrylic acid and/or an alkali metal salt of acrylic acid, and a crosslinking agent is irradiated with ultraviolet rays for polymerization and crosslinking to obtain a water-absorbing resin and molding the resin in a predetermined shape, or the mixture is irradiated with ultraviolet rays for polymerization and crosslinking while holding the mixture in a predetermined shape.

(3) A process wherein an aqueous solution containing an acrylic acid polymer and/or an acrylic acid alkali metal salt polymer, and at least one crosslinking agent selected from among polyepoxy compounds and polyaziridinyl compounds is held in a molding container, and crosslinking the solution at 5° to 50° C. as held in the container.

The production processes (1) and (2) will be described first.

The main monomer unit for forming the molded body of water-absorbing resin of the present invention is at least one of acrylic acid and an alkali metal salt of acrylic acid. According to the present invention, acrylic acid can be used as unneutralized or as neutralized completely to 100%. The alkali metal salt is sodium salt, potassium salt or the like and is obtained by neutralizing acrylic acid with sodium hydroxide, potassium hydroxide or the like. In view of the water-absorbing capacity and strength of the water-absorbing resin, the degree of neutralization is in the range of 50 to 100%, preferably in the range of 60 to 85%, whereas it is desirable to use acrylic acid as unneutralized to ensure a greater SI value (i.e., signal intensity which is thought to be a factor affecting the image) and sharper images for NMR diagnosis. Accordingly, the neutralization degree of acrylic acid is suitably determined in accordance with the condition under which the molded body or resin obtained is used, use thereof, etc.

The crosslinking agent, when copolymerized and/or crosslinked with the monomer, gives a crosslinked structure to the water-absorbing resin obtained. Examples of such crosslinking agents are divinyl compounds, polyepoxy compounds, polyaziridinyl compounds, etc. These agents are used singly, or at least two of them are used in combination.

Examples of useful divinyl compounds are divinylbenzene, N,N'-methylenebisacrylamide, N,N'- methylenebismethacrylamide, polyethylene glycol diacrylate, polypropylene glycol diacrylate and the like.

Examples of polyepoxy compounds are those having at least two epoxy groups such as diglycidyl ethers and triglycidyl ethers. Examples of diglycidyl ethers are (poly)ethylene glycol diglycidyl ether, (poly)propylene glycol diglycidyl ether, 1,6-hexanediol diglycidyl ether, glycerin-1,3-diglycidyl ether, neopentyl glycol diglycidyl ether and the like. Preferable among these are, for example, (poly)ethylene glycol diglycidyl ether and (poly)propylene glycol diglycidyl ether. Preferably, (poly)ethylene glycol diglycidyl ether and the like are about 2 to about 50 in the polymerization degree of alkylene oxide. Examples of triglycidyl ethers are trimethylolpropane triglycidyl ether, glycerin triglycidyl ether and the like. Such compounds having a larger number of functional groups are polyglycerin polyglycidyl ether, sorbitol polyglycidyl ether, pentaerythritol polyglycidyl ether, etc. Preferable among these are trimethylolpropane triglycidyl ether, glycerin triglycidyl ether and polyglycerin polyglycidyl ether. Examples of useful polyepoxy compounds further include epichlorohydrin-modified products of polyamide-polyamine condensates.

Examples of polyaziridinyl compounds are those having at least two azirdinyl groups, such as tetramethylolmethane-tri-$\beta$-aziridinyl propionate, trimethylolpropane-tri-$\beta$-aziridnyl propionate and 4,4'-bis(ethyleneiminocarbonylamino)diphenylmethane.

The amount of crosslinking agent to be used is suitably determined in view of the water-absorbing capacity of the resin to be obtained, gel strength thereof, stability of the gel with time, etc. It is usually about 0.001 to about 5.0 wt. % based on the combined amount of the monomer(s) and crosslinking agent. The amount is preferably 0.005 to 1.0 wt. % especially when the monomer is an alkali metal salt of acrylic acid, or 0.01 to 2.0 wt. % when the monomer is unneutralized acrylic acid. If the amount is less than 0.001 wt. %, a lower gel strength is likely to result, whereas if it is over 5.0 wt. %, the gel tends to become brittle on absorption of water. Thus, amounts outside the specified range are not desirable.

When required, acrylamide, acrylamide-2-methylpropanesulfonic acid salts, lower acrylic acid esters, methacrylic acid, etc. can be used in addition to the essential monomer(s), i.e., acrylic acid and/or acrylic acid alkali metal salt, and crosslinking agent, such compounds are used in an amount of up to about 20 wt. % based on all the monomers in view of the water-absorbing capacity, water retentivity and gel strength of the water-absorbing resin to be obtained.

The photoinitiator to be used is not limited specifically but those already known are usable. Examples of useful photoinitiators are water-soluble azo compounds having an amidino group, such as 2,2'-azobis(N,N'-dimethyleneisobutylamidine) dihydrochloride, 2,2'-azobis(2-amidinopropane) dihydrochloride and 2,2'-azobis(N, N'-dimethyleneisobutylamidine), and photoinitiators generally used for ultraviolet polymerization, such as diacetyl, benzoin, benzil, anthraquinone, acetophenone, diphenyl disulfide, benzophenone and derivatives of these compounds. At least one of these initiators is usable. Among these, the water-soluble azo compounds are desirable in view of the velocity of aqueous solution polymerization of the monomer with ultraviolet rays, radical generating temperature for the polymerization and solubility in the aqueous monomer solution.

However, the kind of photoinitiator to be used is suitably determined depending on whether the mixture to be irradiated with ultraviolet rays is cooled and solidified, and the kind of monomer.

More specifically stated, any of the initiators is usable in the case of the process (1) wherein the monomer used is an acrylic acid alkali metal salt and the mixture is cooled and solidified because no air bubbles occur regardless of the kind of photoinitiator and because almost no monomer remains untreated. On the other hand, in the case of the process (2) wherein the mixture is irradiated with ultraviolet rays without cooling or solidification, the water-soluble azo compound is not suitable to use as the photoinitiator since air bubbles are then likely to occur. In this case, therefore, it is desired to use diacetyl or like photoinitiator which will not produce any gas.

Further when acrylic acid is used as the monomer in either of the processes (1) and (2), it is desirable to use diacetyl or like photoinitiator which will not evolve any gas from the viewpoint of the reaction velocity.

Stated more specifically, the processes (1) and (2) for producing the water-absorbing resin molded body for use in the present invention are practiced in the following manner.

First, specified amounts of acrylic acid and/or acrylic acid alkali metal salt, crosslinking agent and other component monomers which may be used when required are dissolved in water to prepare an aqueous monomer solution. Usually, it is desirable to adjust the monomer concentration of the solution to about 25 to about 65 wt. %, more desirably 30 to 60 wt. %. If the monomer concentration is less than 25 wt. %, the water-absorbing resin obtained is likely to have a lower polymerization degree, whereas if it is over 65 wt. %, the reaction system becomes heated to an excessively high temperature during reaction to produce a water-absorbing resin which is liable to be porous and less likely to have satisfactory water retentivity, hence a disadvantage.

The photoinitiator is then admixed with the aqueous monomer solution with stirring to dissolve the initiator. The amount of photoinitiator to be used is not limited specifically but is usually 0.001 to 5.0 wt. % based on the combined amount of monomers. The amount is preferably 0.01 to 1.0 wt. % when the main monomer is an acrylic acid alkali metal salt, or is preferably 0.05 to 2.0 wt. % when the main monomer is acrylic acid. For polymerization, a water-soluble polymerization initiator such as potassium persulfate can be used in combination with the photoinitiator.

In the case of the production process (1) wherein the mixture is cooled and solidified before irradiation with ultraviolet rays, the mixture is cooled to a temperature not higher than the solidifying point. The solidifying point, which differs, for example, with the monomer concentration, is usually up to 0° C., so that the mixture is cooled to not higher than this temperature. Preferably, the cooling temperature is about −50° to about −30° C.

For example in the case of the production process (1) wherein the mixture is cooled and solidified, the mixture can be molded by solidifying the mixture as placed in a suitable die, container or the like, or by molding the solidified mixture in a suitable die or the like. The mixture molded in a shape in conformity with the contemplated use is polymerized and crosslinked by irradiation with ultraviolet rays after or without removing the molding from the die or the like.

In the case of the production process (2) wherein the mixture is not cooled for solidification, the mixture is irradiated with ultraviolet rays as placed in a die, container or the like for preparing the molding, or the mixture is poured in the form of a sheet onto an endless belt and then irradiated with ultraviolet rays.

Further when required, the molded body thus obtained can be made into various shapes by blanking, cutting or any of other methods.

The mixture is irradiated with ultraviolet rays to initiate polymerization and crosslinking reactions. Insofar as ultraviolet rays are capable of fully penetrate into the mixture, the shape of the molded mixture, die, container or the like is not limited. When required, the irradiation with ultraviolet rays may be conducted with cooling.

To ensure convenience in executing the steps of preparing the molded product, it is desirable to use an endless belt or an open container having a large surface area.

The thickness of the mixture to be irradiated with ultraviolet rays is not limited specifically. For example, even if having a thickness of not smaller than 5 cm, the mixture can be fully polymerized and crosslinked. The amount of ultraviolet rays is usually about 20 to about 3500 mjoules/cm$^2$ although not limited specifically. If the amount is less than this range, insufficient polymerization and crosslinking will result. Amounts exceeding the above range are undesirable since after a crosslinked polymer has been obtained, application of excessive energy is likely to break the crosslinked structure, yielding a low-molecular-weight substance and making the product feel sticky. The amount of radiation is preferably about 20 to about 2000 mjoules/cm$^2$. The source of ultraviolet rays to be used can be any of those already known such as mercury lamp, metal halide lamp and the like and is suitably determined in view of the reaction conditions such as the thickness of the mixture. The wavelength of radiation to be applied is usually 200 to 450 nm although not limited specifically. The application of ultraviolet rays immediately initiates the reactions.

The irradiation time is suitably determined so as to give the above-mentioned amount of radiation. For example when the endless belt is used, the mixture as placed thereon can be allowed to completely react if passed through a location, irradiated under the above condition, over a short period of time which is usually several seconds to several minutes.

Next, the production process (3) will be described.

At least one of an acrylic acid polymer and an acrylic acid alkali metal salt polymer is used in the process (3). Examples of such polymers are those comprising acrylic acid or an alkali metal salt of acrylic acid as the main monomer unit and prepared by various known methods such as aqueous solution polymerization, reverse-phase emulsion polymerization and reverse-phase suspension polymerization. Useful acrylic acid alkali metal salt polymers may be those obtained by preparing an acrylic acid polymer and neutralizing the polymer with an alkali metal salt. Any of such polymers can be used suitably. The aqueous monomer solution to be used for preparing the acrylic acid polymer or acrylic acid alkali metal salt polymer is usually about 3 to about 25 wt. % in monomer concentration. The monomer concentration of the solution is adjusted preferably to 10 to 20 wt. % when the crosslinking agent to be used is a polyepoxy compound or to 3 to 15 wt. % when the agent is a polyaziridinyl compound. If the monomer concentration is lower than 3 wt. %, the water-absorbing resin obtained is likely to have a lower polymerization degree, whereas if it is in excess of 25 wt. %, the reaction system becomes heated to an excessively high temperature during the reaction and is therefore difficult to control in temperature, hence a disadvantage. The neutralization degree of the acrylic acid polymer or acrylic acid alkali metal salt polymer, the kind of alkali metal salt, the kind and amount of optional monomers like those already mentioned, etc. may be the same as in the case of the processes (1) and (2).

The viscosity of aqueous solution of the acrylic acid polymer or acrylic acid alkali metal salt polymer obtained can be determined from the wide range of from about 10 to about 100000 cps. Especially when the crosslinking agent is a polyepoxy compound, the viscosity is preferably about 30000 to about 100000 cps, more preferably about 50000 to about 80000 cps. If the viscosity is lower than 30000 cps, a lower gel strength will result from crosslinking, whereas if it is over 100000 cps, it is difficult to remove air bubbles that would occur before crosslinking. The aqueous solution can be easily adjusted to a viscosity of about 30000 to about 100000 cps usually be adjusting the polymer concentration to about 5 to about 20 wt. %. In the case where the crosslinking agent is a polyaziridinyl compound, the viscosity is preferably about 10 to about 50000 cps, more preferably about 100 to about 10000 cps. If the viscosity is lower than 10 cps, the crosslinking reaction results in a lower gel strength, whereas if it is over 50000 cps, difficulty is encountered in removing air bubbles that would occur before crosslinking. The aqueous solution can be easily adjusted to a viscosity of about 10 to about 50000 cps usually by controlling the polymer concentration to about 3 to about 15 wt. %.

The kind of polyepoxy compounds and polyaziridinyl compounds for use as crosslinking agents is the same as in the processes (1) and (2). When the acrylic acid alkali metal salt polymer is used, either type of crosslinking agent is usable, while the polyaziridinyl compound is preferable to use as the crosslinking agent for the acrylic acid polymer.

The amount of crosslinking agent to be used is suitable determined in view of the water-absorbing capacity and gel strength of the water-absorbing resin to be obtained, the stability of the gel with time, etc.

It is usually about 0.05 to about 5.0 parts by weight, preferably 0.5 to 3.0 parts by weight, per 100 parts by weight of the acrylic acid polymer and/or the acrylic acid alkali metal salt polymer. If the amount is less than 0.05 part by weight, a lower gel strength is likely to result, whereas if it is over 5.0 parts by weight, a brittle gel tends to result. Thus amounts outside the specified range are undesirable.

More specifically, the production process (3) is practiced in the following manner.

First, an aqueous solution or mixture is prepared by mixing an acrylic acid polymer and/or an acrylic acid alkali metal salt polymer, which may usually be in the form of a solution, with at least one crosslinking agent selected from among polyepoxy compounds and polyaziridinyl compounds. The polyaziridinyl compound or the like may be diluted with acetone or the like before mixing. The aqueous solution or mixture is then made substantially free from air bubbles by removing air bubbles therefrom, for example, by subjecting the solution or mixture to a reduced pressure of at least 100 mm Hg to below 760 mm Hg. If the pressure is lower than 100 mm Hg in this case, the solution or mixture is likely to bubble up at a time and spill over the container, whereas the air bubbles are not removable at a pressure of not lower than 760 mm Hg. Alternatively, the air bubbles may be removed one by one with a syringe or the like. It is convenient to remove the air bubbles from the mixture as placed in a molding container.

The mixture free from air bubbles and placed in the molding container is crosslinked at a temperature of about 5° to about 50° C., preferably 15° to 45° C. If the temperature is less than 5° C., the crosslinking reaction will not progress fully, whereas if it is over 50° C., the crosslinking reaction produces water vapor, and air bubbles occur in the molded products. Thus, temperatures outside the specified range are not desirable.

The molding container is not limited specifically but can be any of various shapes in conformity with the contemplated use of the product. For example, die or the like is favorably usable in view of convenience of handling.

In this way, a molded body of water-absorbing resin can be obtained which is substantially free from air bubbles and has high uniformity and transparency and useful strength. When required, the molded body prepared can be made into various shapes by blanking, cutting or any of other methods.

In water content the molded bodies of water-absorbing resin obtained by the proceses (1) and (2) are usually about 35 to about 75 wt. %, and those prepared by the process (3) are usually about 80 to about 97 wt. %. These bodies are generally free from air bubbles and can be handled favorably at room temperature.

Especially, the dry powder of water-absorbing resin forming the molded body obtained by the process (1) has a water-soluble content usually of about 0 to about 7 wt. % when the monomer is an acrylic acid alkali salt or a water soluble content usually of about 0 to about 10 wt. % when the monomer is acrylic acid. Thus the value is extremely smaller than that of conventional water-absorbing resins. Accordingly, the resin has a high polymerization degree and therefore exhibits good stability with time when swollen with water and does not feel sticky.

The dry powder of water-absorbing resin forming the molded body prepared by the process (1), (2) or (3) is comparable to conventional water-absorbing resins in its capacity to absorb pure water when the monomer is an acrylic acid alkali metal salt, and is usually as high as 50 to 500 g/g in this value. On the other hand, when the monomer is acrylic acid, the resin has a lower water absorbing capacity usually of 10 to 100 g/g than when the monomer is the acrylic acid alkali metal salt, but is fully serviceable as a water-absorbing resin.

The molded body of water-absorbing resin obtained is a rubberlike elastic body and has a high gel strength. For example, the gel strength of the molded body obtained by the process (1) or (2) is about 2.5 to about 4 times the gel strength of water-absorbing resin powder as merely swollen with water when the monomer is acrylic acid, or is about 4 to about 8 times the latter strength when the monomer is the acrylic acid alkali metal salt. Further the gel strength of the molded body obtained by the process (3) is about 1.1 to about 3 times the strength when the monomer is acrylic acid or about 1.5 to about 3 times the strength when the monomer is the acrylic acid alkali metal salt.

According to the present invention, a molded body of water-absorbing resin is prepared by one of the foregoing processes in a shape desired for use as a sheet for assisting in NMR diagnosis. The assisting sheet for NMR diagnosis is usually at least 35 wt. %, preferably about 50 to 99 wt. %, in water content. The molded resin body obtained is used as it is or as swollen with water.

Preferably, the NMR diagnosis assisting sheet of the present invention has incorporated therein an alkali metal chloride and/or an alkaline earth metal chloride to supply the alkali metal ion and/or the alkaline earth metal ion to the water-absorbing resin and to obtain NMR images with improved sharpness.

Examples of useful alkali metal chlorides are sodium, potassium and like chlorides. Examples of useful alkaline earth metal chlorides are calcium, magnesium and like chlorides. Although such alkali metal ions and alkaline earth metal ions can be supplied in the form of sulfates, nitrates and like metal salts, it is preferable to use chlorides for the supply of metal ions.

The content of such ions is in the range of concentrations of corresponding ions in the living tissues. The ion content of the molded body of water-absorbing resin is up to about 1000 mmoles, preferably 10 to 40 mmoles, for sodium ion, up to about 250 mmoles, preferably 3 to 10 mmoles, for potassium ion, up to about 5 mmoles, preferably 0.5 to 2 mmoles, for calcium ion, up to about 25 mmoles, preferably 0.25 to 1 mmole, for magnesium ion, or up to about 1000 mmoles, preferably 8 to 32 mmoles, for chlorine ion. Metal ion contents and chlorine ion contents exceeding the above ranges give images of reduced sharpness and are therefore undesirable. From the viewpoint of sharpness of NMR images, it is desired to use all the four kinds of metal ions exemplified above.

The NMR diagnosis assisting sheet of the present invention gives improved sharpness to NMR images when further incorporating therein a paramagnetic metal and/or an alcohol.

Examples of useful paramagnetic metals are gadolinium, nickel, copper, manganese, titanium, vanadium, chromium, cobalt, iron and the like. These paramagnetic metals are supplied in the form of water-soluble metal salts such as sulfates, nitrates, acetates and chelate compounds. The paramagnetic metal is used in an amount of up to 10 wt. %, preferably up to 5 wt. %, based on the weight of the resin in the molded body. Amounts in excess of 10 wt. % are not desirable since obscure NMR images will then be obtained.

The method of incorporating metal ions into the molded body of water-absorbing resin is not limited specifically. For example, the following methods are useful. In the case of the molded body obtained by the process (1) or (2), metal ions are incorporated into an aqueous solution for polymerizing the molded body. Alternatively, the molded body prepared is swollen with an aqueous solution containing metal ions. In the case of the molded body obtained by the process (3), metal ions are incorporated into the aqueous solution for preparing the molded body by crosslinking, or into an aqueous alkali solution for neutralizing the aqueous solution of polyacrylic acid or an aqueous solution for adjusting the concentration of the acid solution. Alternatively, the molded body prepared is swollen with an aqueous solution containing metal ions.

Furthermore, ethyl alcohol, glycerin or like alcohol is usable singly or in combination with metals such as those mentioned above for the sheet of the invention.

Although the method of incorporating the alcoholic compound into the molded body of water-absorbing resin is not limited specifically, the alcoholic compound is usually added to the aqueous solution for adjusting the water content of the molded body obtained and is thereby incorporated into the molded body. The concentration of the alcoholic compound in the aqueous solution is usually up to 30 wt. %. The molded body of water-absorbing resin can be made to contain usually up to 300 wt. % of the alcoholic compound based on the weight of the resin. The amount is preferably up to 100 wt. %.

The NMR diagnosis assisting sheet of the present invention made of the molded body of water-absorbing resin is used, for example, by the following methods.

The sheet is affixed directly to the human body (e.g., of patient) over the region (e.g., affected part or lesion) of which NMR images are to be obtained, or is placed into a known plastics bag which will not affect magnetism and then affixed to the contemplated region, followed by NMR diagnosis. Alternatively, the sheet is installed within an NMR apparatus for NMR diagnosis.

The present invention has the following outstanding advantages.

(i) Use of the sheet of the present invention readily provides sharp images for the NMR diagnosis of various regions of the living body, such as the heart and liver, without changing heart beat although it has been difficult to obtain sharp NMR images of such organs.

(ii) The molded body of water-absorbing resin forming the present sheet has a sufficient gel strength for use in NMR diagnosis. The sheet has good stability at room temperature, remains free of changes, for example, in strength despite the lapse of time and is easy to handle.

The present invention will be described in greater detail with reference to the following examples and test example, whereas the invention is in no way limited to these examples.

In the examples, the molded bodies were checked for occurrence of air bubbles, transparency and strength by the following methods.

Air bubbles

The molded body obtained was checked with the unaided eye for the presence or absence of air bubbles according to the following criteria.

A: No air bubbles.
B: Up to 3 air bubbles, not larger than about 0.1 cm in diameter, were found per 1 cm$^3$.
C: Numerous air bubbles were found.

Transparency

The water-containing gel of the molded body obtained was swollen with water to a water content of 95% and then made into a 1-cm-thick test piece, which was thereafter placed on paper bearing Arabic numerals printed with 14-point types. The test piece was checked as to whether the Arabic numerals were legible with the unaided eye according to the following criteria.

A: High transparency, and all the Arabic numerals were legible.
B: The numerals were difficult to read owing to air bubbles.
C: Totally illegible.

Strength

The molded body of water-absorbing resin was swollen with pure water to a water content of 95% and then tested for strength using Neo Curdmeter, product of IIO ELECTRIC CO.

EXAMPLE 1

To 300 g of acrylic acid and 389.3 g of water was added 121.6 g (corresponding to 75 mole % based on acrylic acid) of sodium hydroxide with ice-cooling for neutralization. N,N'-Methylenebisacrylamide (crosslinking agent, hereinafter referred to as "MBAM") was dissolved in an amount of 0.06 g (0.016 wt. % based on the combined amount of the monomers) in the solution, and nitrogen gas was thereafter introduced into the resulting solution to drive out dissolved oxygen. With the solution adjusted to a temperature of 10° C., 2,2'-azobis(N,N'-dimethyleneisobutylamidine) dihydrochloride (photoinitiator, product of WAKO PURE CHEMICAL INDUSTRIES, LTD., brand name: "VA-044") was further dissolved in an amount of 0.10 g (0.027 wt. % based on the combined amount of all monomers) in the solution to obtain an adjusted solution containing the monomers in a combined concentration of 46 wt. %.

The adjusted solution (283 g) was placed into a glass container, 246 mm in length, 195 mm in width and 30 mm in depth and irradiated with ultraviolet rays by a device (produced by EYE GRAPHIC CO., LTD. and having two 2-KW high-pressure mercury lamps, 80 W/cm, wavelength 250 nm) in an amount of 900 mjoules/cm$^2$ for 5 minutes to obtain a molded body of water-containing gel crosslinked copolymer (water-absorbing resin) having a thickness of 0.5 cm and rubberlike elasticity.

The molded body was checked for air bubbles with the result of C and for transparency with the result of B, and was $12.3 \times 10^4$ dynes/cm$^2$ in strength.

The molded body was caused to absorb 150 g of deionized water and placed into a nylon bag, which was then sealed off and allowed to stand for 2 days to obtain an NMR diagnosis assisting sheet, 290 mm in length, 230 mm in width and 5.9 mm in thickness, according to the invention.

EXAMPLES 2 AND 3

NMR diagnosis assisting sheets were prepared in the same manner as in Example 1 with the exception of changing the amount of deionized water to be absorbed by the molded body and the period of standing of the bagged body as listed in Table 1.

EXAMPLE 4

An NMR diagnosis assisting sheet was prepared in the same manner as in Example 3 except that the metal ion supplying compounds listed in Table 1 were added in the listed amounts to the deionized water to be absorbed by the molded body.

EXAMPLE 5

A molded body of water-containing gel crosslinked copolymer was prepared in the same manner as in example 1 except that the adjusted solution (566 g) obtained in Example 1 was placed into a glass container, 246 mm in length, 195 mm in width and 30 mm in depth, and allowed to stand in a constant-temperature chamber at −20° C. for 2 hours for solidification and molding.

The molded body was checked for air bubbles with the result of A and for transparency with the result of A, and was $21.6 \times 10^4$ dynes/cm$^2$ in strength.

The molded body was caused to absorb 301 g of deionized water and placed into a nylon bag, which was then sealed off and allowed to stand for 2 days to obtain an NMR diagnosis assisting sheet, 290 mm in length, 230 mm in width and 11.8 mm in thickness, according to the invention.

EXAMPLES 6-8

NMR diagnosis assisting sheets were prepared in the same manner as in Example 5 with the exception of changing the amount of adjusted solution, the amount of deionized water to be absorbed by the molded body and the period of standing of the bagged body as listed in Table 1.

EXAMPLES 9-13

NMR diagnosis assisting sheets were prepared in the same manner as in Example 5 except that the metal ion supplying compounds listed in Table 1 were used in the listed amounts in preparing the aqueous solution of sodium acrylate monomer of Example 5.

EXAMPLE 14

An NMR diagnosis assisting sheet was prepared in the same manner as in example 5 with the exception of adding 0.82 g of $NiSO_4 \cdot 6H_2O$ to the adjusted solution and causing the resulting molded body to absorb 5% aqueous solution of ethanol instead of deionized water.

EXAMPLE 15

An NMR diagnosis assisting sheet was prepared in the same manner as in Example 5 with the exception of adding 0.42 ml of meglumine gadopentetate (brand name: "Magnevist," product of SCHERING of Germany) to the adjusted solution.

EXAMPLE 16

To 300 g of acrylic acid were added 352 g of water and 0.15 g of MBAM (0.05 wt. % based on the combined amount of the monomers) to prepare a solution, into which nitrogen gas was introduced to drive out dissolved oxygen. With the solution adjusted to a temperature of 10° C., Darocur 1173 (product of MERCK JAPAN LTD.) was further added in an amount of 0.90 g (0.3 wt. % based on all monomers) to the solution to obtain an adjusted solution containing the monomers at a combined concentration of 46 wt. %.

A molded body of water-containing gel crosslinked copolymer was prepared in the same manner as in example 1 except that the adjusted solution (566 g) prepared above was placed into a glass container, 246 mm in length, 195 mm in width and 30 mm in depth, and allowed to stand in a constant-temperature chamber at −20° C. for 2 hours for solidification and molding.

The molded body was checked for air bubbles with the result of A and for transparency with the result of A, and was $6 \times 10^4$ dynes/cm² in strength.

The molded body was caused to absorb 301 g of deionized water and placed into a nylon bag, which was then sealed off and allowed to stand for 2 days to obtain an NMR diagnosis assisting sheet, 290 mm in length, 230 mm in width and 11.8 mm in thickness, according to the invention.

EXAMPLE 17

An NMR diagnosis assisting sheet was prepared in the same manner as in Example 5 except that the metal ion supplying compounds listed in Table 1 were used in the listed amounts in preparing the same aqueous solution of sodium acrylate monomer as used in Example 16 to use this solution in placed of the corresponding solution of Example 5.

EXAMPLE 18

A 200 g quantity of acrylic acid and 1030 g of deionized water were placed into a 2-liter flask equipped with a stirrer, thermometer, condenser and nitrogen supply tube. The solution was heated to 60° C., and a solution of 0.73 g of ammonium persulfate in 2 g of deionized water was added to the solution to initiate polymerization with cooling. Upon the temperature of the solution rising to 70° C. owing to the heat of polymerization, 80 g of deionized water was further added so as to control the solution to a maximum temperature of 90° to 95° C. When the temperature of the solution dropped, the supply of nitrogen was discontinued to effect polymerization. Two hours thereafter, a solution of 0.025 g of hydroquinone in 1 g of deionized water was added to the reaction mixture to complete the polymerization.

To 1314 g of the resulting aqueous solution of polyacrylic acid was added a solution of 82 g of sodium hydroxide in 1026 g of deionized water to obtain an aqueous solution of sodium salt of polyacrylic acid having a nonvolatile content of 10% and a neutralization degree of 75%.

The aqueous solution of sodium polyacrylate (696 g) and 2.09 g of polyethylene glycol diglycidyl ether (brand name: "EPOLIGHT 400E," product of KYO-EISHA CHEMICAL CO., LTD., 3 wt. % based on all monomers) were placed into a glass container measuring 290 mm in length, 230 mm in width and 30 mm in depth, stirred and thereafter allowed to stand at 10° C. and 300 mm Hg for 24 hours, followed by removal of air bubbles. Subsequently, the mixture was allowed to stand in a constant-temperature chamber at 40° C. for 3 days, affording a molded body of water-containing gel crosslinked copolymer measuring 290 mm in length, 230 mm in width and 10 mm in thickness, i.e., an NMR diagnosis assisting sheet of the invention.

The molded body was checked for air bubbles with the result of A and for transparency with the result of A, and was $2.4 \times 10^4$ dynes/cm² in strength.

EXAMPLES 19-20

NMR diagnosis assisting sheets were prepared in the same manner as in Example 18 with the exception of changing the amount of deionized water to be absorbed by the molded body and the period of standing as listed in Table 1.

EXAMPLE 21

An NMR diagnosis assisting sheet was prepared in the same manner as in Example 18 except that the metal ion supplying compounds listed in Table 1 were used in the listed amounts in preparing the aqueous solution of sodium acrylate monomer.

EXAMPLE 22

Deionized water (1150 g) was added to 1314 g of the aqueous solution of polyacrylic acid obtained in Example 18 to obtain an aqueous solution of polyacrylic acid having a nonvolatile content of 8%.

The aqueous solution of sodium salt of polyacrylic acid (696 g) was placed into a glass container measuring 290 mm in length, 230 mm in width and 30 mm in depth, a solution of 1.11 g of TAZO (tetramethylolmethanetri-β-aziridinyl propionate, product of SOGO PHARMACEUTICAL CO., LTD.) in 20.09 g of acetone was slowly added to the solution with stirring, and the mixture was allowed to stand at 10° C. for 1 hour. After removing air bubbles from the surface of the mixture with a syringe, the mixture was allowed to stand at 10° C. and 300 mm Hg for 24 hours for further removal of air bubbles. The mixture was then placed into a constant-temperature chamber at 20° C. for 3 days to obtain a molded body of water-containing gel crosslinked copolymer measuring 290 mm in length, 230 mm in width and 10 mm in thickness, i.e., an NMR diagnosis assisting sheet of the invention.

The molded body was checked for air bubbles with the result of A and for transparency with the result of A, and was $2.6 \times 10^4$ dynes/cm$^2$ in strength.

EXAMPLE 23

An NMR diagnosis assisting sheet was prepared in the same manner as in Example 22 except that the metal ion supplying compounds listed in Table 1 were used in the listed amounts in preparing the aqueous solution of sodium acrylate monomer.

TEST EXAMPLE 1

NMR diagnosis was conducted in the following manner using the sheets of the invention obtained in Examples 1 to 23.

The sheet to be tested was affixed to the chest of the human body, and the chest was photographed using an NMR diagnosis apparatus, 1.5 T in magnetic field intensity and 64.91 MHz in resonance frequency (product of Toshiba, Model MRT-200/RX). The measurement was made by the field echo method under the conditions that the time of pulse repetition was 50 msec, the time of echo was 15 msec and the Flip angle was 30°, using rephase to rearrange the signals for the components of bloodstream.

The results are given in Table 1, the column of "Sharpness of image." The sharpness was determined with the unaided eye according to the following criteria.

5: Image elements were distinguishable with high clarity of detail.
4: Image elements were roughly distinguishable with fair clarity of detail.
3: Image elements were roughly distinguishable but obscure in detail.
2: Image elements were roughly distinguishable but undistinguishable in detail.
1: Obscure image.

Figure 2:
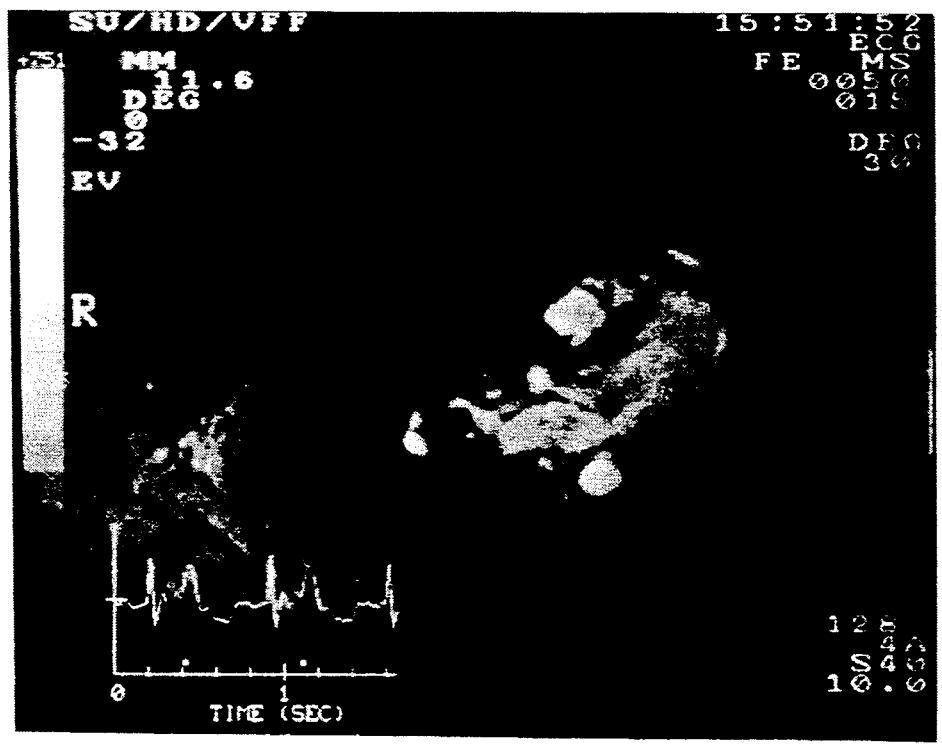

FIGS. 1 and 2 show examples of actual NMR images. FIG. 1 is a photograph of an NMR image (evaluated as 5) showing a human body in section and obtained using the sheet of Example 9 according to the invention. FIG. 2 is a photograph of an NMR image (evaluated as 1) showing the human body in section and obtained without using any sheet or the like for comparison.

TEST EXAMPLE 2

A phantom, $30 \times 30 \times 30$ cm, which was a container of acrylic resin containing oil for babies, was used in place of the human body, and the sheet was tested under the same conditions as in Test Example 1 to measure the SI value (signal intensity) of the phantom.

Table 1 shows the additives and production conditions for the sheets obtained in Examples, and the results of evaluation of the NMR images obtained with use of the sheets.

TABLE 1

| Ex. | Amount of chloride added (g) | | | | NiSO$_4$.6H$_2$O (g) | Maglumine gadopentetate (ml) |
|---|---|---|---|---|---|---|
| | NaCl | KCl | CaCl$_2$.2H$_2$O | MgCl$_2$.6H$_2$O | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0.406 | 0.122 | 0.024 | 0.017 | 0 | 0 |
| 5 | 0 | 0 | 0 | 0 | 0 | 0 |
| 6 | 0 | 0 | 0 | 0 | 0 | 0 |
| 7 | 0 | 0 | 0 | 0 | 0 | 0 |
| 8 | 0 | 0 | 0 | 0 | 0 | 0 |
| 9 | 0.748 | 0.230 | 0.045 | 0.031 | 0 | 0 |
| 10 | 1.496 | 0.230 | 0.045 | 0.031 | 0 | 0 |
| 11 | 0.148 | 0.450 | 0.045 | 0.031 | 0 | 0 |
| 12 | 0.748 | 0.230 | 0.090 | 0.031 | 0 | 0 |
| 13 | 0.748 | 0.230 | 0.045 | 0.062 | 0 | 0 |
| 14 | 0 | 0 | 0 | 0 | 0.82 | 0 |
| 15 | 0 | 0 | 0 | 0 | 0 | 0.42 |
| 16 | 0 | 0 | 0 | 0 | 0 | 0 |
| 17 | 0.748 | 0.230 | 0.045 | 0.031 | 0 | 0 |
| 18 | 0 | 0 | 0 | 0 | 0 | 0 |
| 19 | 0 | 0 | 0 | 0 | 0 | 0 |
| 20 | 0 | 0 | 0 | 0 | 0 | 0 |
| 21 | 2.706 | 0.814 | 0.163 | 0.112 | 0 | 0 |
| 22 | 0 | 0 | 0 | 0 | 0 | 0 |
| 23 | 2.165 | 0.651 | 0.130 | 0.090 | 0 | 0 |

| Ex. | Monomer temp. (°C.) | Absorbed liquid (g) | | Period of standing (days) | Amount of adjusted solution | Water content (%) | Thickness of sheet (mm) | Sharpness of image | SI value |
|---|---|---|---|---|---|---|---|---|---|
| | | Amount of deionized water | 5% Ethanol aqueous solution | | | | | | |
| 1 | 10 | 150 | — | 0 | 283 | 70 | 5.9 | 2 | 352 |
| 2 | 10 | 1017 | — | 0 | 283 | 90 | 8.5 | 3 | 373 |
| 3 | 10 | 150 | — | 90 | 283 | 70 | 5.9 | 2 | 352 |
| 4 | 10 | 150 | — | 0 | 283 | 70 | 5.9 | 4 | 364 |
| 5 | −20 | 301 | — | 0 | 566 | 70 | 11.8 | 4 | 381 |
| 6 | −20 | 150 | — | 0 | 283 | 70 | 5.9 | 3 | 379 |

TABLE 1-continued

| 7  | −20 | 2034 | —   | 0  | 566 | 90 | 17.1 | 3 | 386 |
|----|-----|------|-----|----|-----|----|------|---|-----|
| 8  | −20 | 301  | —   | 90 | 566 | 70 | 11.8 | 4 | 381 |
| 9  | −20 | 301  | —   | 0  | 566 | 70 | 11.8 | 5 | 392 |
| 10 | −20 | 301  | —   | 0  | 566 | 70 | 11.8 | 4 | 388 |
| 11 | −20 | 301  | —   | 0  | 566 | 70 | 11.8 | 4 | 389 |
| 12 | −20 | 301  | —   | 0  | 566 | 70 | 11.8 | 4 | 390 |
| 13 | −20 | 301  | —   | 0  | 566 | 70 | 11.8 | 4 | 390 |
| 14 | −20 | —    | 301 | 0  | 566 | 70 | 11.8 | 5 | 317 |
| 15 | −20 | 301  | —   | 0  | 566 | 70 | 11.8 | 5 | 308 |
| 16 | −20 | 301  | —   | 0  | 566 | 70 | 11.8 | 5 | 492 |
| 17 | −20 | 301  | —   | 0  | 566 | 70 | 11.8 | 5 | 498 |
| 18 | —   | 1026 | —   | 0  | 696 | 90 | 10.0 | 3 | 311 |
| 19 | —   | 219  | —   | 0  | 696 | 85 | 10.0 | 3 | 299 |
| 20 | —   | 1026 | —   | 90 | 696 | 90 | 10.0 | 3 | 311 |
| 21 | —   | 1026 | —   | 0  | 696 | 90 | 10.0 | 4 | 325 |
| 22 | —   | 1150 | —   | 0  | 696 | 92 | 10.0 | 5 | 505 |
| 23 | —   | 1150 | —   | 0  | 696 | 92 | 10.0 | 5 | 507 |

Table 1 and FIGS. 1 and 2 reveal that very sharp NMR images can be obtained using the sheets of the present invention.

We claim:

1. An NMR diagnosis assisting sheet characterized in that the sheet comprises a molded body of a water-absorbing resin, the water-absorbing resin forming a uniform matrix phase wherein the molecules of the resin are interlocked with one another, and water absorbed by the resin is uniformly dispersed as chemically or physically bonded to the resin.

2. A sheet as defined in claim 1 which contains an alkali metal ion or an alkaline earth metal ion.

3. A sheet as defined in claim 1 which contains a paramagnetic metal or an alcoholic compound.

4. A sheet as defined in claim 1 wherein the water-absorbing resin is a crosslinked product of an acrylic acid polymer or a crosslinked product of an acrylic acid alkali metal salt polymer.

5. A sheet as defined in claim 1 wherein the molded body is at least 5 mm in thickness.

6. A sheet as defined in claim 1 wherein the sheet is at least about 35 wt. % in water content.

* * * * *